United States Patent
Sadavarte et al.

(10) Patent No.: US 12,233,167 B2
(45) Date of Patent: Feb. 25, 2025

(54) BIO-COMPATIBLE POLYURETHANE MICROCAPSULES AND PROCESS FOR THE PREPARATION THEREOF

(71) Applicant: COUNCIL OF SCIENTIFIC & INDUSTRIAL RESEARCH, New Delhi (IN)

(72) Inventors: Nilakshi Vaibhav Sadavarte, Pune (IN); Kadhiravan Shanmuganathan, Pune (IN); Parshuram Gajanan Shukla, Pune (IN)

(73) Assignee: Council of Scientific & Industrial Research, New Delhi (IN)

( * ) Notice: Subject to any disclaimer, the term of this patent is extended or adjusted under 35 U.S.C. 154(b) by 718 days.

(21) Appl. No.: 17/601,583

(22) PCT Filed: Mar. 27, 2020

(86) PCT No.: PCT/IN2020/050289
§ 371 (c)(1),
(2) Date: Oct. 5, 2021

(87) PCT Pub. No.: WO2020/202187
PCT Pub. Date: Oct. 8, 2020

(65) Prior Publication Data
US 2022/0202731 A1    Jun. 30, 2022

(30) Foreign Application Priority Data
Apr. 5, 2019    (IN) .............. 201911013812

(51) Int. Cl.
| | |
|---|---|
| *A61K 9/50* | (2006.01) |
| *A01N 25/10* | (2006.01) |
| *A01N 25/28* | (2006.01) |
| *A01N 37/10* | (2006.01) |
| *A01N 37/18* | (2006.01) |
| *A01N 43/70* | (2006.01) |
| *A01N 47/30* | (2006.01) |
| *A61K 9/48* | (2006.01) |
| *A61K 31/11* | (2006.01) |
| *A61K 31/192* | (2006.01) |
| *A61K 31/555* | (2006.01) |
| *B01J 13/16* | (2006.01) |

(52) U.S. Cl.
CPC ............ *A61K 9/5031* (2013.01); *A01N 25/10* (2013.01); *A01N 25/28* (2013.01); *A01N 37/10* (2013.01); *A01N 37/18* (2013.01); *A01N 43/70* (2013.01); *A01N 47/30* (2013.01); *A61K 9/4866* (2013.01); *A61K 9/5089* (2013.01); *A61K 31/11* (2013.01); *A61K 31/192* (2013.01); *A61K 31/555* (2013.01); *B01J 13/16* (2013.01)

(58) Field of Classification Search
CPC .. A61K 9/5031; A61K 9/4866; A61K 9/5089; A61K 31/11; A61K 31/192; A61K 31/555; A01N 25/10; A01N 25/28; A01N 37/10; A01N 37/18; A01N 43/70; A01N 47/30; B01J 13/16

See application file for complete search history.

US012233167B2

(56) References Cited

U.S. PATENT DOCUMENTS

| | | |
|---|---|---|
| 5,962,003 A | 10/1999 | Shukla et al. |
| 2006/0251688 A1 | 11/2006 | Gajanan et al. |
| 2013/0196071 A1 | 8/2013 | Yang et al. |
| 2018/0042825 A1* | 2/2018 | Lei .................... A61K 8/84 |

FOREIGN PATENT DOCUMENTS

WO    WO 2015/023961    2/2015

OTHER PUBLICATIONS

Kulkami et al. Applied Science and advanced Material International 2(1); 7-10 (2015).*
Ashraf M.A., et al.: Effectiveness of silica based sol-gel microencapsulation method for odorants and flavors leading to sustainable environment, Frontiers in Chemistry, vol. 3, 2015, 42, 1-15 https://www.frontiersin.org/article/10.3389/fchem.2015.00042.
Azizi N., et al.: Isosorbide-based microcapsules for cosmetotextiles, Industrial Crops and Products, vol. 52, 2014, pp. 150-157, ISSN 0926-6690, https://doi.org/10.1016/j.indcrop.2013.10.027.
Gabriel L. P., et al.: Synthesis and Characterization of Bio-Based Polyurethane for Tissue Engineering Applications, Chem. Eng. Trans. 2016, vol. 49, pp. 349-354.
Gaudin F. and Sintes-Zydowicz N., "Core-shell biocompatible polyurethane nanocapsules obtained by interfacial step polymerisation in miniemulsion", Colloids And Surfaces A: Physicochemical And Engineering Aspects, vol. 331, 2008, pp. 133-142.
Genç, E. , Alay Aksoy, S. "Fabrication of Microencapsulated PCMs With Nanoclay Doped Chitosan Shell and Their Application to Cotton Fabric". Textile and Apparel 26 (2016 ): 180-188 https://dergipark.org.tr/en/pub/tekstilvekonfeksiyon/issue/23652/251956.
Kulkarni S.S., et al., "Polyurea and Polyurethane Microcapsules Containing Mosquito Repellent DEET: Preparation and Characterization", Applied Science And Advanced Materials International, vol. 2(1), 2015, pp. 7-10.
Patil M., et al.: Tuning Controlled Release Behavior of Starch Granules Using Nanofibrillated Cellulose Derived from Waste Sugarcane Bagasse, ACS Sustainable Chem. Eng, 2018.

(Continued)

*Primary Examiner* — Shirley V Gembeh
(74) *Attorney, Agent, or Firm* — Norton Rose Fulbright US LLP (57) ABSTRACT

The present invention relates to partially bio-based and bio-compatible polyurethane microcapsules. More particularly, the present invention relates to partially bio-based and bio-compatible polyurethane microcapsules for sustained release of an active ingredient. The present invention also relates to a process for the preparation of the partially bio-based and bio-compatible polyurethane microcapsules.

10 Claims, 11 Drawing Sheets

(56) References Cited

OTHER PUBLICATIONS

Shinde S.A., et al., "Release of Ibuprofen-Na from Polyurethane microcapsules prepared with different diols", 2006.
Sooyoul, P., & Koh, E.: The synthesis of polyurethane microcapsules and evaluation of self-healing paint protection properties, 2017.
Yoo Y., et al.: Sustained Dye Release Using Poly(urea-urethane)/Cellulose Nanocrystal Composite Microcapsules. Langmuir 2017, 33, 1521-1532, ACS Appl. Mater. Interfaces 2017, 33 (6), 1521-1532.

* cited by examiner

BIO-COMPATIBLE POLYURETHANE MICROCAPSULES AND PROCESS FOR THE PREPARATION THEREOF

CROSS-REFERENCE TO RELATED APPLICATIONS

This application is a national phase application under 35 U.S.C. § 371 of International Application No. PCT/IN2020/050289 filed 27 Mar. 2020, which claims priority to Indian patent application No. 201911013812 filed 5 Apr. 2019. The entire contents of each of the above-referenced disclosures is specifically incorporated herein by reference without disclaimer.

FIELD OF THE INVENTION

The present invention relates to partially bio-based and bio-compatible polyurethane microcapsules. More particularly, the present invention relates to partially bio-based and bio-compatible polyurethane microcapsules for sustained release of an active ingredient and the process for preparation thereof.

BACKGROUND OF THE INVENTION AND PRIOR ART

Bio-based polymers are materials which are produced from renewable resources. The synthesis of polymers from renewable resources has attracted attention of researchers throughout the globe because of escalating cost of petrochemicals, increasing demand and concern regarding depletion of the mineral oil sources along with political and environmental concerns. Most of the polymeric shell materials used for encapsulation of active core by interfacial polymerization are based on petroleum feed stock.

Article titled "Isosorbide-based microcapsules for cosmeto-textiles" by N Azizi et al. published in *Industrial Crops and Products;* 2014, Volume 52, pp 150-157 reports new microcapsules based on renewable materials and containing perfume designed for cosmeto-textile application. Such microcapsules contained neroline fragrance as a core material and bio-based polyurethane as a wall material. The polymer wall was synthesized by interfacial polycondensation of isosorbide and methylene bis(phenyl isocyanate). The chemical structure of the microcapsules was confirmed by IR and $^1$H NMR spectroscopies. The encapsulation efficiency of perfume was determined using $^1$H NMR analysis technique, which accounts for 30% which is very low for commercial viability.

Polyurethane microcapsules by interfacial polymerization of toluene 2,4-diisocyanate (TDI) or 4,4-diphenylmethane diisocyanate (MDI) with diol for encapsulation of waterborne polyurethane (PU) paint is disclosed in "The synthesis of polyurethane microcapsules and evaluation of self-healing paint protection properties" by Sooyoul, Park et. al published in 21st International Conference on Composite Materials in 2017.

Aromatic diisocyanates such as methylene bis(phenyl isocyanate) or toluene diisocyanate are routinely used in synthesis of polyurethanes. A major limitation in use of aromatic diisocyanates in the field of microencapsulation is toxicity of degradation products causing harm to the environment. However, polyurethanes based on aliphatic diisocyanates are considered as more biocompatible than polyurethanes based on aromatic isocyanates because the products of degradation of aromatic isocyanates are toxic, such as aromatic amines (Chem. Eng. Trans. 2016, 49, 349-354).

The Research article titled 'Tuning Controlled Release Behavior of Starch Granules Using Nanofibrillated Cellulose Derived from Waste Sugarcane Bagasse' by Parshuram G. Shukla et. al published in ACS Sustainable Chem. Eng in May, 2018 provides controlled release formulations (CRFs) to encapsulate agrochemicals for sustained release, wherein the CRFs are prepared from cellulose nanofibres (CNFs) derived from waste sugarcane bagasse mixed with gelatinized maize starch and urea formaldehyde to yield nano composite granular formulation. Dimethyl phthalate (DMP) is used as model encapsulant. In recent years, nanoparticulates such as nanoclay (J. Text. App. 2016, 26, 180-188.), nanocellulose (Langmuir 2017, 33, 1521-1532, ACS Appl. Mater. Interfaces 2017, 9, 31763-31776) and nanosilica (Front. Chem. 2015, 3, 42, 1-15) have been employed to enhance the barrier properties and attain further reduction in release of active ingredient from CRFs. These investigations have mainly focused on core shell nanocomposite microcapsules having non-biobased polymer wall made of polyurea or polyurethane.

Owing to increasing environmental awareness and rapid oil feedstock depletion, the exploitation of renewable resource materials for synthesis of polymeric shell materials is the current need in the field of microencapsulation.

Therefore, there is still a need in the art to provide bio-based polyurethane microcapsules that can achieve high encapsulation efficiency and sustained release rate using bio-sourced materials.

Objective of the Invention

The primary objective of the present invention is to provide a partially bio-based and bio-compatible polyurethane microcapsules having a polymeric wall made up of a bio-based diol and an aliphatic diisocyanate.

Another objective of the present invention is to provide a process for the preparation of a partially bio-based and bio-compatible polyurethane microcapsules by using simple, interfacial polymerization which is relatively cost effective and conducive to scale up.

SUMMARY OF THE INVENTION

Accordingly, the present invention provides a partially bio-based and bio-compatible polyurethane microcapsules for sustained release of an active ingredient comprising;
  i) a core containing at least one active ingredient;
  ii) a bio-compatible polymeric shell consisting of (a) a bio-based aliphatic diol, (b) an aliphatic diisocyanate, (c) a cross-linker and (d) an additive;
wherein, the partially bio-based and bio-compatible polyurethane microcapsule has an encapsulation efficiency of 70-95% and sustained release rate of the active ingredient.

The active ingredient is selected from the group consisting of perfumes, biocides, pharmaceuticals, pesticides, enzymes, chemical reagents, self-healing agent and the like in an amount ranging from 30 to 80% w/w based on the total weight of the microcapsules.

In a preferred embodiment, the active ingredient is selected from the group consisting of dimethyl phthalate, N,N-Diethyl-meta-toluamide (DEET), Ibuprofen, Diuron, Zinc Pyrithione, Irgarol, and 4-Anisaldehyde.

The aliphatic diisocyanate is selected from the group consisting of Isophoronediisocyanate (IPDI), pentamethylenediisocyanates (PDI), 1,6 Hexamethylenediisocyanates (HMDI) and 4,4'-Diisocyanatodicyclohexylmethane ($H_{12}$ MDI).

The bio-based aliphatic diol is selected from the group consisting of isosorbide, 1,3-propane diol, 1,4-butane diol, 2,3-butane diol, and 1,6-hexane diol.

The mole ratio of diisocyanate to hydroxyl groups present in aliphatic diol is 1.2:1.

The cross-linker is selected from the group consisting of glycerol, trimethylol propane (TMP), triethylenetetramine (TETA) and trimethylol ethane (TME) in an amount of 5 to 20 wt % based on the weight of diol.

The additive is selected from nanoparticulates such as nanocellulose, nanoclay, nanosilica and carbon nanotube (CNT) in an amount ranging from 2 to 6 wt % based on the total weight of monomers.

In another aspect, the present invention provides a general interfacial polymerization process for the preparation of partially bio-based and bio-compatible polyurethane microcapsules comprising the steps of:
 a) preparing a solution of additive in water by overnight stirring followed by homogenization to obtain a dispersion;
 b) adding the dispersion prepared in step (a) to a solution of a surfactant in water followed by sonicating to obtain a continuous phase;
 c) emulsifying a solution of aliphatic diisocyanate and an active ingredient in the continuous phase obtained in step (b) to obtain a first mixture;
 d) preparing a second mixture of a bio-based aliphatic diol, a cross-linker and a catalyst in water;
 e) adding the second mixture obtained in step (d) dropwise to the first mixture obtained in step (c) to obtain a reaction mixture; and
 f) stirring the reaction mixture of step (e) followed by centrifugation and filtration to obtain the partially bio-based and bio-compatible polyurethane microcapsules.

The surfactant in the process is selected from the group consisting of polyvinyl pyrrolidone (PVP K-90), polyvinyl pyrrolidone (PVP K-30), Polyvinyl alcohol (PVA), Tween 80, sodium lignosulphonate (SLS) and sodium dodecyl sulfate (SDS) in an amount of 3 to 5% (w/v) based on the continuous phase.

DETAILED DESCRIPTION OF THE INVENTION

The invention will now be described in detail in connection with certain preferred and optional embodiments, so that various aspects thereof may be more fully understood and appreciated.

The present invention provides polyurethane microcapsules for controlling the release of an active ingredient wherein the polymeric wall of the microcapsule is formed using bio-based diols and aliphatic diisocyanates. The polyurethane microcapsules of the present invention are biocompatible thereby eliminating the toxic products formed after degradation of the bio-based polymeric wall. Further, the polyurethane microcapsules are prepared by simple, cost effective interfacial polymerization which ensures direct control of the mean size and thickness of the capsules and high active loading with tunable delivery processes.

In an embodiment, the present invention provides partially bio-based and bio-compatible polyurethane microcapsules for sustained release of an active ingredient comprising;
 i) a core containing at least one active ingredient;
 ii) a bio-compatible polymeric shell consisting of (a) a bio-based diol, (b) an aliphatic diisocyanate, (c) a cross linker and (d) an additive;
wherein the partially bio-based and bio-compatible polyurethane microcapsule has an encapsulation efficiency of 70-95% and sustained release rate of the active ingredient.

The aliphatic diisocyanate is selected from the group consisting of isophorone diisocyanate (IPDI), pentamethylene diisocyanates (PDI), 1, 6 Hexamethylene diisocyanates (HMDI) and 4,4'-Diisocyanatodicyclohexylmethane ($H_{12}$ MDI).

The bio-based aliphatic diol is selected from the group consisting of isosorbide, 1,3-propane diol, 1,4-butane diol, 2,3-butane diol, and 1,6-hexane diol.

The molar ratio of diisocyanate to hydroxyl groups present in aliphatic diol is 1.2:1.

The active ingredient is selected from the group consisting of perfumes, biocides, pharmaceuticals, pesticides, enzymes, chemical reagents, self-healing agent and the like in an amount of 30 to 80 wt % based on total weight of microcapsules.

In preferred embodiment, the active ingredient is selected from the group consisting of dimethyl phthalate (DMP), N,N-Diethyl-meta-toluamide (DEET), Ibuprofen, Diuron, Zinc Pyrithione, Irgarol, and 4-Anisaldehyde.

The cross linker is selected from the group consisting of glycerol, trimethylol propane (TMP), triethylenetetramine (TETA) and trimethylol ethane (TME) in an amount ranging from 5 to 20 wt % based on the weight of diol.

The additive is selected from nanoparticulates such as nanocellulose, nanoclay, nanosilica and carbon nanotube (CNT) in an amount ranging from 2 to 6 wt % based on weight of polymer wall.

In another embodiment, the present invention provides a general interfacial polymerization process for the preparation of partially bio-based and bio-compatible polyurethane microcapsules comprising the steps:
a) preparing a solution of additive in water by overnight stirring followed by homogenization to obtain a dispersion;
b) adding the dispersion prepared in step (a) to a solution of a surfactant in water followed by sonicating to obtain a continuous phase;
c) emulsifying a solution of aliphatic diisocyanate and an active ingredient in the continuous phase obtained in step (b) to obtain a first mixture;
d) preparing a second mixture of a bio-based aliphatic diol, a cross-linker and a catalyst in water;
e) adding the second mixture obtained in step (d) drop-wise to the first mixture obtained in step (c) to obtain a reaction mixture; and
f) stirring the reaction mixture of step (e) followed by centrifugation and filtration to obtain the partially bio-based and bio-compatible polyurethane microcapsules.

The additive is selected from the group consisting of nanocellulose, nanoclay, nanosilica and carbon nanotube (CNT).

The aliphatic diisocyanate is selected from the group consisting of isophorone diisocyanate (IPDI), pentamethylene diisocyanates (PDI), 1,6 Hexamethylene diisocyanates (HMDI) and 4,4'-Diisocyanatodicyclohexylmethane ($H_{12}$ MDI).

The bio-based aliphatic diol is selected from the group consisting of isosorbide, 1,3-propane diol, 1,4-butane diol, 2,3-butane diol, and 1,6-hexane diol.

The surfactant is selected from the group consisting of polyvinyl pyrrolidone (PVP K-90), polyvinyl pyrrolidone (PVP K-30), polyvinyl alcohol (PVA), Tween 80, sodium lignosulphonate (SLS) and sodium dodecyl sulfate (SDS).

The cross-linker is selected from the group consisting of glycerol, trimethylol propane (TMP), triethylenetetramine (TETA) and trimethylol ethane (TME).

The catalyst is selected from the group consisting of 1,4-Diazabicyclo[2.2.2]octane (DABCO), and Dibutyltin-Dilaurate (DBTDL).

The active ingredient is selected from the group consisting of perfumes, biocides, pharmaceuticals, pesticides, enzymes, chemical reagents, self-healing agent and the like.

In a preferred embodiment, the active ingredient is selected from the group consisting of dimethyl phthalate, N,N-Diethyl-meta-toluamide (DEET), Ibuprofen, Diuron, Zinc Pyrithione, Irgarol, and 4-Anisaldehyde.

Accordingly, a solution of additive in water was prepared by overnight stirring followed by homogenization and was added to a solution of surfactant in water to obtain a continuous phase. To this continuous phase, a solution of aliphatic diisocyanate and an active ingredient was added and stirred at 1000 rpm and 27° C. to obtain a first mixture. A solution of a bio-based aliphatic diol, a cross-linker and a catalyst in water was prepared separately as a second mixture and added drop-wise to the first mixture containing a diisocyanate and an active ingredient at 1000 rpm and 27° C. and continued to stir for 4 hours at 30° C. After continuing the stirring at 50° C. at 500 rpm for 2 hours, the reaction mixture was centrifuged and the obtained polyurethane microcapsules were filtered and dried.

In a preferred embodiment, the present invention discloses partially bio-based and bio-compatible polyurethane microcapsules for sustained release of an active ingredient comprising;
i) a core containing dimethyl phthalate as an active ingredient in an amount ranging from 30 to 80 wt % based on total weight of the microcapsules and
ii) a polymeric shell consisting of isophorone diisocyanate and a bio-based isosorbide, glycerol as a cross linker in an amount of 5 to 20 wt % based on the weight of isosorbide, and nanocellulose as an additive in an amount of 2 to 6 wt % based on polymer weight;
wherein, the partially bio-based and bio-compatible polyurethane microcapsule has an encapsulation efficiency of 70-95% and sustained release rate of the active ingredient.

The molar ratio of isophorone diisocyanate to hydroxyl groups present in aliphatic diol is 1.2:1.

In another preferred embodiment, the process for the preparation of bio-based polyurethane microcapsules by using interfacial polymerization is depicted in Scheme 1 below:

Scheme 1: Synthesis of polyurethane by interfacial polymerization

In an embodiment, the polyurethane microcapsules loaded with 50% DMP and 2-4 wt % of an additive i.e. nanocellulose of the present invention are spherical in shape with average size of 2-25μ.

Figure 8:
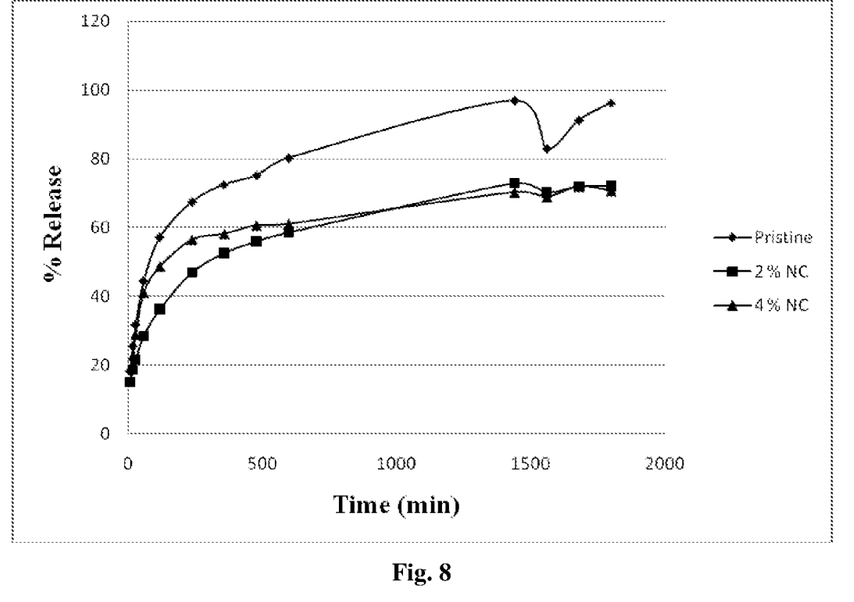
FIG. 8: Release rate study of microcapsules obtained in Example 2, Example 3 and Example 4.

The partially bio-based and bio-compatible polyurethane microcapsules of the present invention containing nanocellulose shows sustained release rate of the active ingredient DMP, in comparison to the pristine microcapsules (MIC's). The microcapsules containing 2% nanocellulose exhibited significant reduction in the release rate of DMP in the first 500 min as compared to MICs containing 4% nanocellulose (FIG. 8).

EXAMPLES

The following examples, which include preferred embodiments, will serve to illustrate the practice of this invention, it being understood that the particulars shown are by way of example and for purpose of illustrative discussion of preferred embodiments of the invention.

Materials: Dimethyl phthalate (99%), Isophorone diisocyanate (98%) (IPDI), 1, 4-Diazabicyclo (2, 2, 2) octane (98%) (DABCO) were purchased from Sigma Aldrich, USA. Methanol (HPLC grade, 99.7%) and Glycerol were purchased from Merck Ltd, India. Polyvinyl pyrrolidone (K90, LR) (PVP) was obtained from S. D. Fine Chemical Ltd, India. Isosorbide was a gift sample obtained from Reliance Company. Nanocellulose fibrils were isolated from waste sugarcane bagasse in the laboratory. Distilled water was used as a continuous medium. All other chemicals were used as received.

Figure 1:
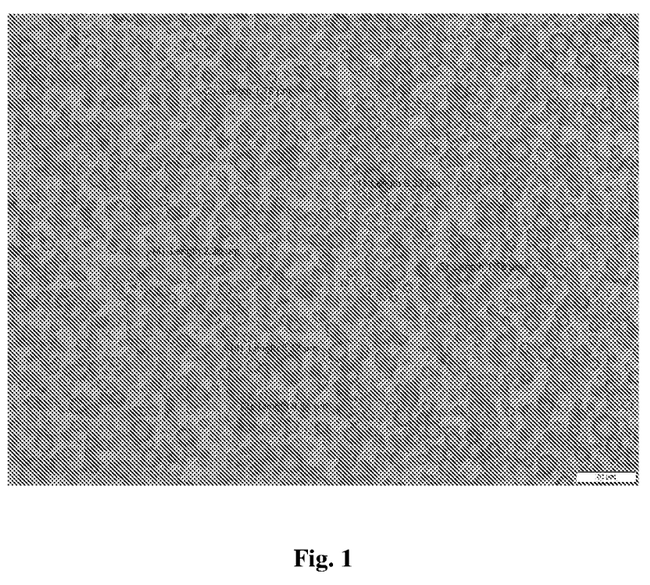
FIG. 1: Optical micrograph of microcapsules obtained in Example 1

Example 1: Preparation of Blank Microcapsules 1.25 g of surfactant PVP K90 (5% w.r.t continuous medium) was dissolved in 25 mL of distilled water in a 250 mL beaker by sonicating the mixture for 30 minutes. To this surfactant solution, 2.7 g of IPDI was added while stirring the mixture at 1000 rpm (revolutions per minute) using turbine type stirrer at 27° C. Then a mixture of 1 g of isosorbide, 0.2 g of glycerol and 0.022 g of DABCO in 4 mL of distilled water was added drop wise over a period of 10 min. The reaction mixture was continued to stir at 30° C. for 4 hours at 1000 rpm and at 50° C. for 2 hours at 500 rpm. The reaction mixture was centrifuged and filtered and the obtained residue was dried in air draft oven at 45° C. The yield of microcapsules obtained was 89%. FIG. 1 shows the optical micrograph of microcapsules obtained.

Figure 2:
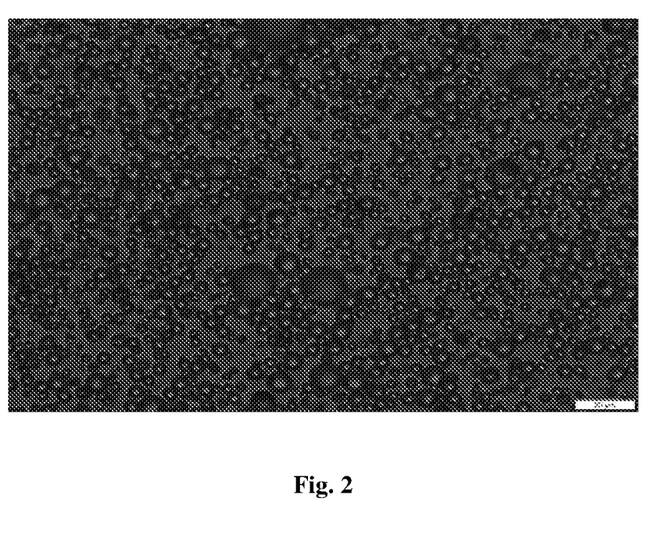
FIG. 2: Optical micrograph of microcapsules obtained in Example 2
Figure 5A:
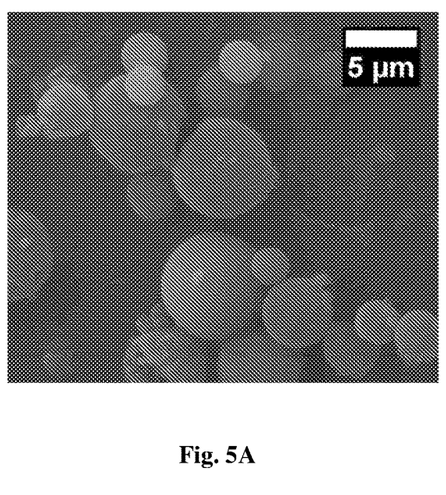
FIG. 5A-5C: SEM image of microcapsules obtained in Example 2
Figure 5B:
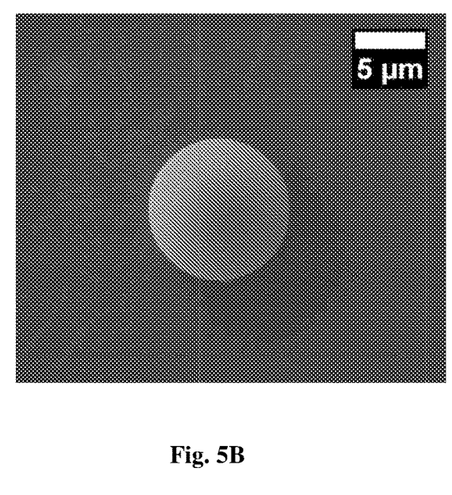
Figure 5C:
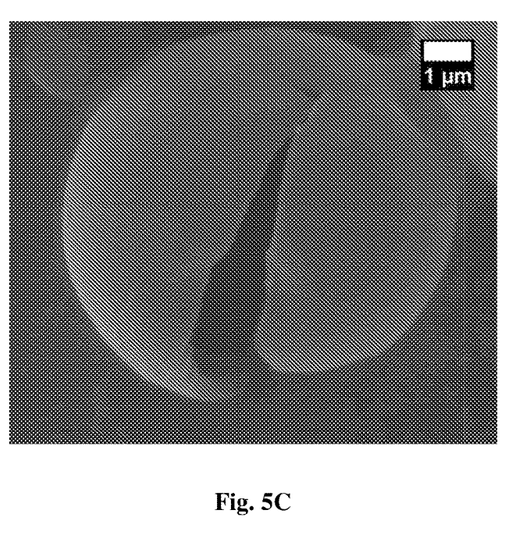

Example 2: Preparation of Polyurethane Microcapsules (Pristine Microcapsules) Containing Dimethyl Phthalate (DMP) with 50% Loading 2.0 g of surfactant PVP K90 (5% w.r.t continuous medium) was dissolved in 40 g of distilled water in 250 mL beaker by sonicating the mixture for 30 minutes. To this surfactant solution, mixture of 3.45 g of DMP and 2.7 g of IPDI was added while stirring the mixture at 1000 rpm (revolutions per minute) using turbine type stirrer at 27° C. Then, a mixture of 1 g of isosorbide, 0.2 g of glycerol and 0.022 g of DABCO in 4 mL of distilled water was added drop wise over a period of 10 min. The reaction mixture was continued to stir at 30° C. for 4 hours at 1000 rpm and at 50° C. for 2 hours at 500 rpm. The reaction mixture was centrifuged and filtered and the obtained residue was dried in air draft oven at 45° C. The yield of microcapsules obtained was 66.32%. FIG. 2 shows the optical micrograph of microcapsules obtained. FIGS. 5A-5C show the SEM image of microcapsules obtained.

Figure 3:
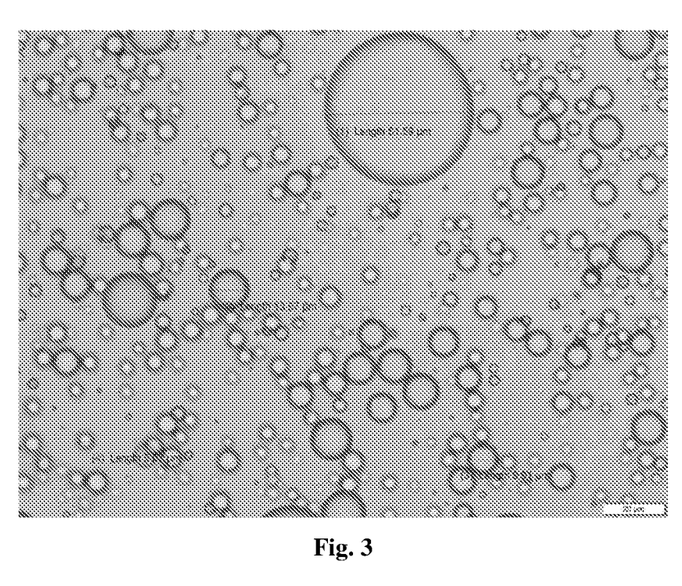
FIG. 3: Optical micrograph of microcapsules obtained in Example 3
Figure 6A:
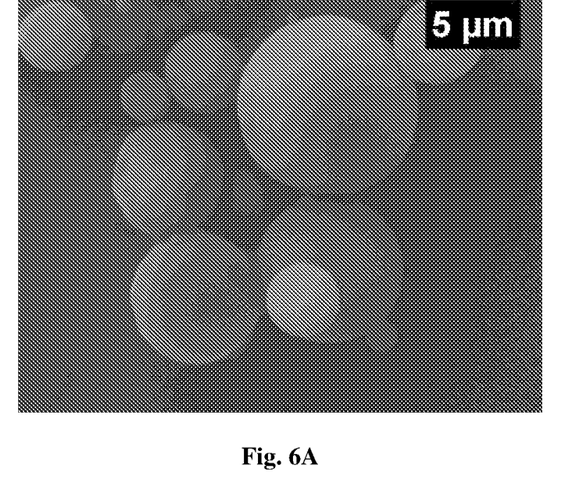
FIG. 6A-6B: SEM image of microcapsules obtained in Example 3
Figure 6B:
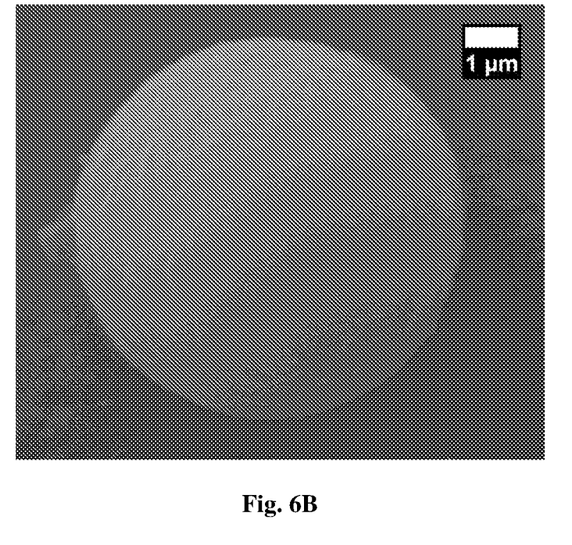

Example 3: Preparation of Polyurethane Microcapsules Containing Nanocellulose (2% NC) as an Additive and Dimethyl Phthalate (DMP) with 50% Loading 0.078 g of nanocellulose (2% w.r.t. polymer wall) was dispersed in 10 mL of distilled water and was added to a surfactant solution of PVP K90 (5% w.r.t continuous medium) prepared by adding 2.0 g of surfactant in 30 g of distilled water in 250 mL beaker. To this solution, a mixture of 3.45 g of DMP and 2.7 g of IPDI was added while stirring the mixture at 1000 rpm (revolutions per minute) using turbine type stirrer at 27° C. Then, a mixture of 1 g of isosorbide, 0.2 g of glycerol and 0.022 g of DABCO in 4 mL of distilled water was added drop wise over a period of 10 min. The reaction mixture was continued to stir at 30° C. for 4 hours at 1000 rpm and at 50° C. for 2 hours at 500 rpm. The reaction mixture was centrifuged and filtered and the obtained residue was dried in air draft oven at 45° C. The yield of microcapsules obtained was 68.58%. FIG. 3 shows the optical micrograph of microcapsules obtained. FIGS. 6A-6B show the SEM image of microcapsules obtained.

Figure 4:
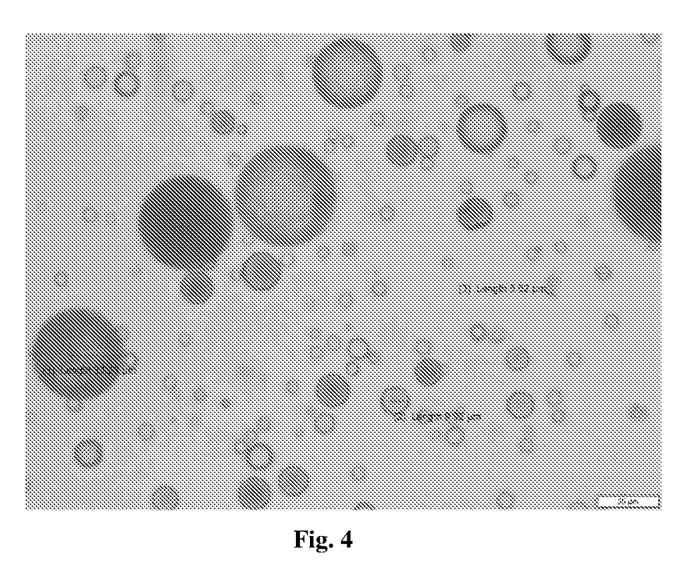
FIG. 4: Optical micrograph of microcapsules obtained in Example 4
Figure 7A:
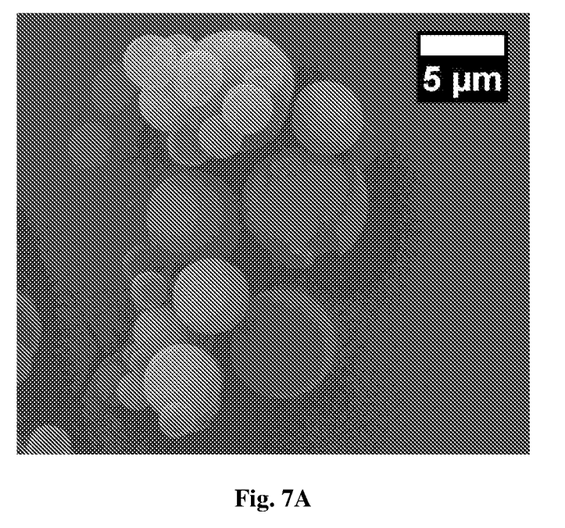
FIG. 7A-7B: SEM image of microcapsules obtained in Example 4
Figure 7B:
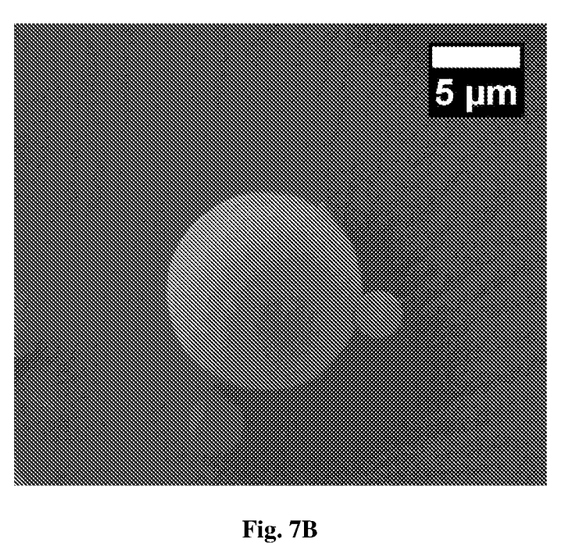

Example 4: Preparation of Polyurethane Microcapsules Containing Nanocellulose (4% NC) as an Additive and Dimethyl Phthalate (DMP) with 50% Loading 0.156 g of nanocellulose (4% w.r.t. polymer wall) was dispersed in 10 mL of distilled water and was added to a surfactant solution of PVP K90 (5% w.r.t continuous medium) prepared by adding 2.0 g of surfactant in 30 g of distilled water in 250 mL beaker. To this solution, a mixture of 3.45 g of DMP and 2.7 g of IPDI was added while stirring the mixture at 1000 rpm (revolutions per minute) using turbine type stirrer at 27° C. Then, a mixture of 1 g of isosorbide, 0.2 g of glycerol and 0.022 g of DABCO in 4 mL of distilled water was added drop wise over a period of 10 min. The reaction mixture was continued to stir at 30° C. for 4 hours at 1000 rpm and at 50° C. for 2 hours at 500 rpm. The reaction mixture was centrifuged and filtered and the obtained residue was dried in air draft oven at 45° C. The yield of microcapsules obtained was 62.22%. FIG. 4 shows the optical micrograph of microcapsules obtained. FIGS. 7A-7B show the SEM image of microcapsules obtained.

Figure 9:
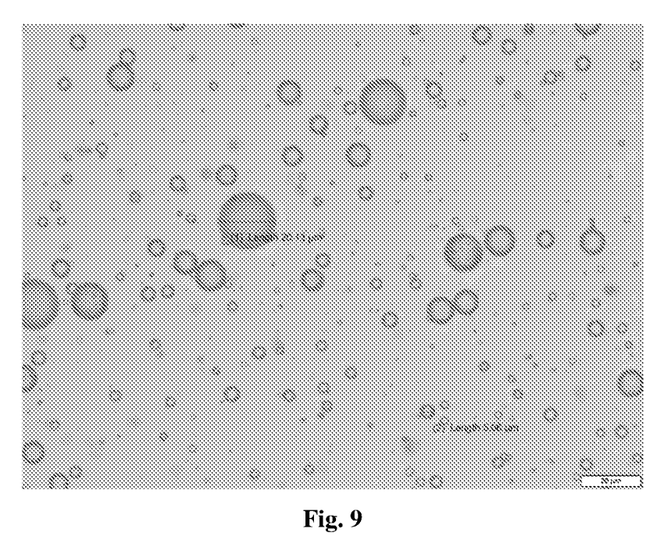
FIG. 9: Optical micrograph of microcapsules obtained in Example 5
Figure 12A:
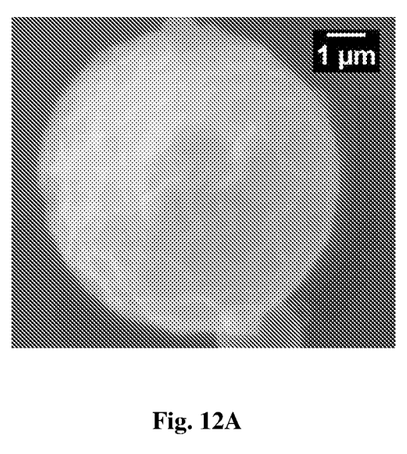
FIG. 12A-12C: SEM image of microcapsules obtained in Example 5
Figure 12B:
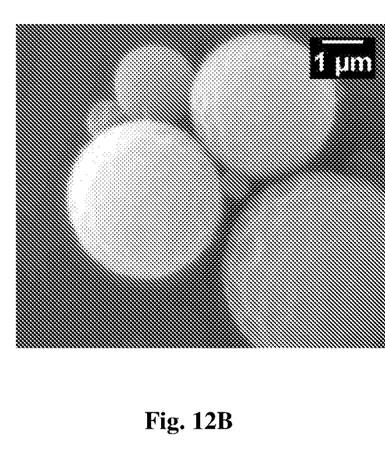
Figure 12C:
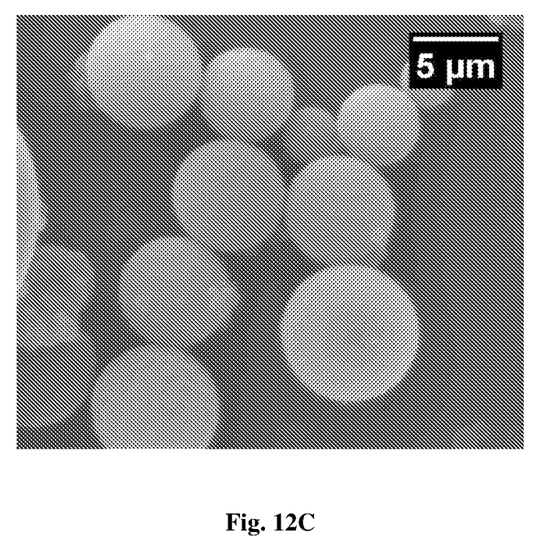
Figure 13A:
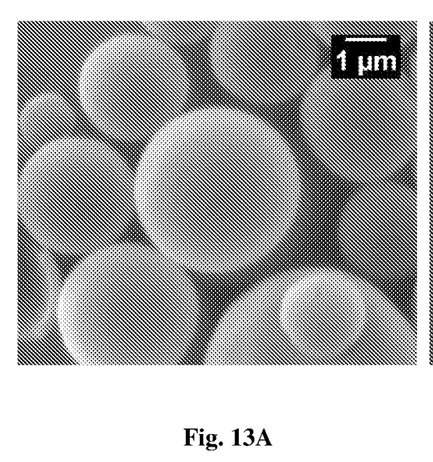
FIG. 13A-13C: SEM image of microcapsules obtained in Example 6
Figure 13B:
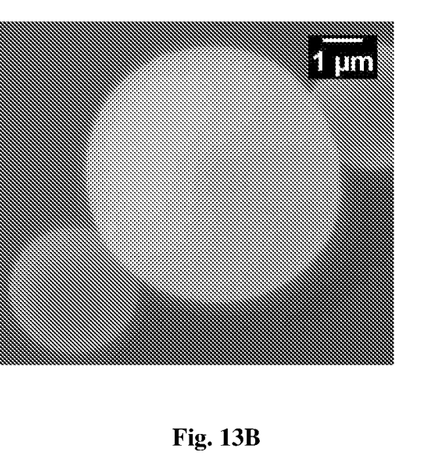
Figure 13C:
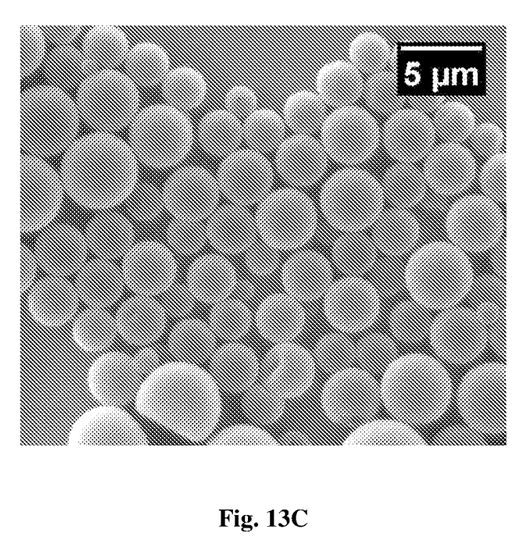

Example 5: Preparation of Polyurethane Microcapsules (Pristine Microcapsules) Containing Dimethyl Phthalate (DMP) with 40% Loading: 2.0 g of Surfactant PVP K90 (5% w.r.t continuous medium) was dissolved in 40 g of distilled water in 250 mL beaker by sonicating the mixture for 30 minutes. To this surfactant solution, a mixture of 2.30 g of DMP and 2.7 g of IPDI was added while stirring the mixture at 1000 rpm (revolutions per minute) using turbine type stirrer at 27° C. Then, a mixture of 1 g of isosorbide, 0.2 g of glycerol and 0.022 g of DABCO in 4 mL of distilled water was added drop wise over a period of 10 min. The reaction mixture was continued to stir at 30° C. for 4 hours at 1000 rpm and at 50° C. for 2 hours at 500 rpm. The reaction mixture was centrifuged and filtered and the obtained residue was dried in air draft oven at 45° C. The yield of microcapsules obtained was 64.66%. FIG. 9 shows the optical micrograph of microcapsules obtained. FIGS. 12A-12C show the SEM image of microcapsules obtained.

Figure 10:
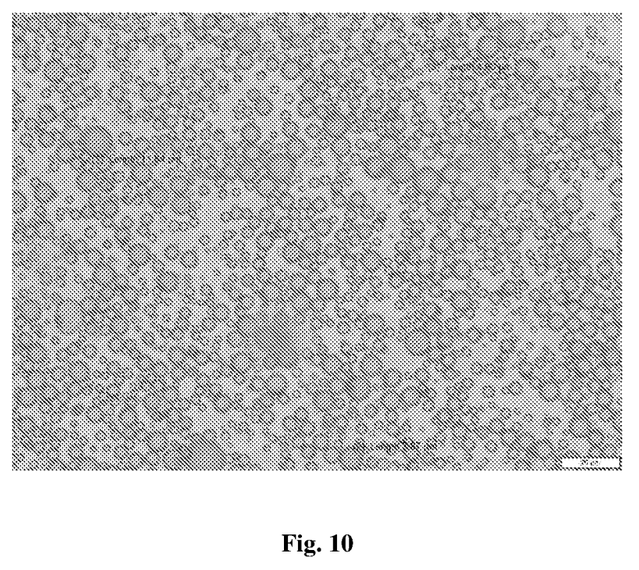
FIG. 10: Optical micrograph of microcapsules obtained in Example 6

Example 6: Preparation of Polyurethane Microcapsules (Pristine Microcapsules) Containing Dimethyl Phthalate (DMP) with 60% Loading 2.0 g of surfactant PVP K90 (5% w.r.t continuous medium) was dissolved in 40 g of distilled water in 250 mL beaker by sonicating the mixture for 30 minutes. To this surfactant solution, a mixture of 5.17 g of DMP and 2.7 g of IPDI was added while stirring the mixture at 1000 rpm (revolutions per minute) using turbine type stirrer at 27° C. Then, mixture of 1 g of isosorbide, 0.2 g of glycerol and 0.022 g of DABCO in 4 mL of distilled water was added drop wise over a period of 10 min. The reaction mixture was continued to stir at 30° C. for 4 hours at 1000 rpm and at 50° C. for 2 hours at 500 rpm. The reaction mixture was centrifuged and filtered and the obtained residue was dried in air draft oven at 45° C. The yield of microcapsules obtained was 71.75%. FIG. 10 shows the optical micrograph

Figure 11:
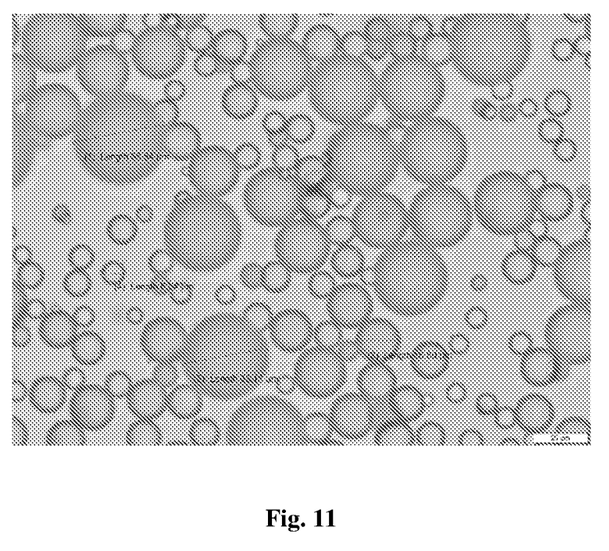
FIG. 11: Optical micrograph of microcapsules obtained in Example 7

Example 7: Preparation of Polyurethane Microcapsules (Pristine Microcapsules) Containing Dimethyl Phthalate (DMP) with 70% Loading 2.0 g of surfactant PVP K90 (5% w.r.t continuous medium) was dissolved in 40 g of distilled water in 250 mL beaker by sonicating the mixture for 30 minutes. To this surfactant solution, a mixture of 8.06 g of DMP and 2.7 g of IPDI was added while stirring the mixture at 1000 rpm (revolutions per minute) using turbine type stirrer at 27° C. Then, a mixture of 1 g of isosbide, 0.2 g of glycerol and 0.022 g of DABCO in 4 mL of distilled water was added drop wise over a period of 10 min. The reaction mixture was continued to stir at 30° C. for 4 hours at 1000 rpm and at 50° C. for 2 hours at 500 rpm. After the completion of the reaction, free DMP was seen in the dispersion. FIG. 11 shows the optical micrograph of microcapsules obtained.

Figure 14:
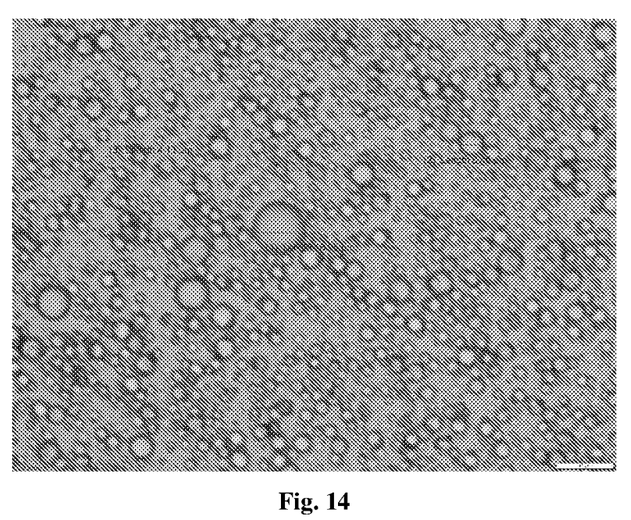
FIG. 14: Optical micrograph of microcapsules obtained in Example 8

Example 8: Preparation of Polyurethane Microcapsules (Pristine Microcapsules) from 1,4 Butane Diol (BDO) and Isophorone Diisocyanate (IPDI) Containing Dimethyl Phthalate (DMP) with 50% Loading 2.0 g of surfactant PVP K90 (5% w.r.t continuous medium) was dissolved in 40 g of distilled water in 250 mL beaker by sonicating the mixture for 30 minutes. To this surfactant solution, a mixture of 4.71 g of DMP and 3.51 g of IPDI was added while stirring the mixture at 1000 rpm (revolutions per minute) using turbine type stirrer at 27° C. Then, a mixture of 1 g of 1,4 butane diol, 0.2 g of glycerol and 0.022 g of DABCO in 4 mL of distilled water was added drop wise over a period of 10 min. The reaction mixture was continued to stir at 30° C. for 4 hours at 1000 rpm and at 50° C. for 2 hours at 500 rpm. The reaction mixture was centrifuged and filtered and the obtained residue was dried in air draft oven at 45° C. The yield of microcapsules obtained was 82.57%. FIG. 14 shows the optical micrograph of microcapsules obtained.

Figure 15:
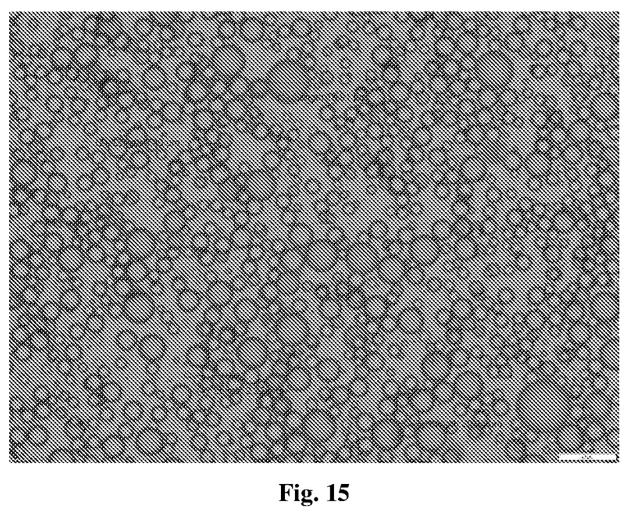
FIG. 15: Optical micrograph of microcapsules obtained in Example 9

Example 9: Preparation of Polyurethane Microcapsules (Pristine Microcapsules) from 1,4 Butane Diol (BDO) and Isophorone Diisocyanate (IPDI) Containing Dimethyl Phthalate (DMP) with 70% Loading 2.0 g of surfactant PVP K90 (5% w.r.t continuous medium) was dissolved in 40 g of distilled water in 250 mL beaker by sonicating the mixture for 30 minutes. To this surfactant solution, a mixture of 11.0 g of DMP and 3.51 g of IPDI was added while stirring the mixture at 1000 rpm (revolutions per minute) using turbine type stirrer at 27° C. Then, a mixture of 1 g of 1,4 butane diol, 0.2 g of glycerol and 0.022 g of DABCO in 4 mL of distilled water was added drop wise over a period of 10 min. The reaction mixture was continued to stir at 30° C. for 4 hours at 1000 rpm and at 50° C. for 2 hours at 500 rpm. The reaction mixture was centrifuged and filtered and the obtained residue was dried in air draft oven at 45° C. The yield of microcapsules obtained was 94.19%. FIG. 15 provides the optical micrograph of microcapsules obtained.

Figure 16:
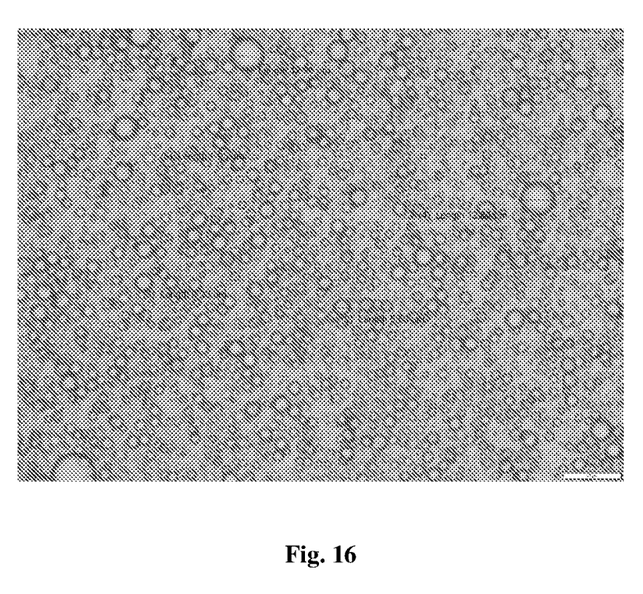
FIG. 16: Optical micrograph of microcapsules obtained in Example 10

Example 10: Preparation of Polyurethane Microcapsules (Pristine Microcapsules) from 1,4 Butane Diol (BDO)+1,1,1-Tris(Hydroxymethyl)Propane (as a Cross-Linker) (TMP) and Isophorone Diisocyanate (IPDI) Containing N,N-Diethyl-Meta-Toluamide (DEET) with 50% Loading 2.0 g of surfactant PVP K90 (5% w.r.t continuous medium) was dissolved in 40 g of distilled water in 250 mL beaker by sonicating the mixture for 30 minutes. To this surfactant solution, a mixture of 4.53 g of DEET and 3.33 g of IPDI was added while stirring the mixture at 1000 rpm (revolutions per minute) using turbine type stirrer at 27° C. Then, a mixture of 1 g of 1,4 butane diol, 0.2 g of TMP and 0.022 g of DABCO in 4 mL of distilled water was added drop wise over a period of 10 min. The reaction mixture was continued to stir at 30° C. for 4 hours at 1000 rpm and at 50° C. for 2 hours at 500 rpm. The reaction mixture was centrifuged and filtered and the obtained residue was dried in air draft oven at 45° C. The yield of microcapsules obtained was 70.60%. FIG. 16 shows the optical micrograph of microcapsules obtained.

Experimental Data:

| Experiment No. | DMP % Loading | Additive % | Particle Size (micron) | Yield* | Encapsulation Efficiency (%) |
|---|---|---|---|---|---|
| Example 1 | — | — | 2-10 | 89% | — |
| Example 2 | 50% | — | 2-25 | 66.32% | 93.24 |
| Example 3 | 50% | 2% | 2-25 | 68.58% | 80.28 |
| Example 4 | 50% | 4% | 2-25 | 62.22% | 70.26 |
| Example 5 | 40% | — | 2-25 | 64.66 | 91.20 |
| Example 6 | 60% | — | 2-25 | 71.75 | 86.71 |
| Example 7 | 70% | — | 2-15 | # | # |

*% Yield was calculated by filtration method,
Free DMP seen in the dispersion

Experimental Details for Examples 8 to 10:

| Example No. | Diol | Diisocyanate | Active | % Loading | Cross-linker | Particle Size (micron) | Yield* % | Encapsulation Efficiency (%) |
|---|---|---|---|---|---|---|---|---|
| 8 | 1,4 Butane diol | IPDI | DMP | 50% | Glycerol | 2-25 | 82.57 | 92.24 |
| 9 | 1,4 Butane diol | IPDI | DMP | 70% | Glycerol | 2-25 | 94.19 | 86.91 |
| 10 | 1,4 Butane diol | IPDI | DEET | 50% | TMP | 2-25 | 70.60 | 79.81 |

*% Yield was calculated by filtration method

Example 11

Characterization of Pristine Microcapsules (MICs)

Olympus BX-60, USA optical microscope fitted with Olympus SC30 digital camera was used to measure the size of MICs. SEM (E-SEM, Quanta 200-3D) at 15 kV was used to study the morphology of MICs. Samples were drop casted on silicon-wafer and sputter coated with gold prior to imaging to avoid charging. FT-IR spectra were recorded using ATR mode on a Perkin-Elmer Spectrum GX spectrophotometer. $^1$H-NMR spectra were recorded on a Bruker NMR spectrophotometer (400 MHz) in DMSO-$d_6$ solution at 27° C. UV-visible spectrophotometer (Hitachi model 220) was used to study the release of DMP from MICs.

1. Optical Microscopy and SEM

Obtained microcapsules (aqueous dispersion) were observed through optical microscope to determine their size and size distribution. Optical micrographs of blank polyurethane microcapsules (Example 1), pristine MICs (Example 2) and MIC-NC (2 wt %) (Example 3). Optical micrographs of all the synthesized batches exhibited the spherical shape of the MICs and the average size of all the MICs were in the range of 2 to 25 microns. SEM photographs of (a) pristine MICs (Example 2) (b) MIC-NC (2 wt %) (Example 3) and MIC-NC (4 wt %) has been presented in the FIGS. 4 to 6. The morphology of the polyurethane microcapsules exhibited the spherical shape.

2. FT-IR and $^1$H-NMR Study:

FT-IR spectra were recorded using ATR mode on a Perkin-Elmer Spectrum GX spectrophotometer. FT-IR spectrum of pristine MICs exhibited the presence of characteristic frequencies of DMP (1722 cm$^{-1}$ due to —C═O, 1273 and 1121 cm$^{-1}$ due to ester group) along with urethane characteristics frequencies (3327 cm$^{-1}$ corresponding to —N—H, 1730 cm$^{-1}$ due to —C═O, 1070 cm$^{-1}$ due to —C—O—C) whereas blank microcapsules of polyurethanes indicated only urethane characteristics frequencies. This indicated the encapsulation of DMP by polyurethane as a wall material.

$^1$H-NMR spectra were recorded on a Bruker NMR spectrophotometer (400 MHz) in DMSO-$d_6$ solution at 27° C.

Example 1 (Blank microcapsules of polyurethane)$^1$H-NMR (400 MHz, DMSO-$d_6$): δ (ppm) 5.77 (d, 1H, —NH), 5.57 (d, 1H, —NH), 3.67 (s, 2H, —CH$_2$—NH), 2.75-0.77 (combined signals corresponding to —CH$_3$, —CH$_2$, —CH of isosorbide and IPDI).

Dimethyl phthalate δ (ppm): 7.74-7.69 (d, 4 Ar—H), 3.82 (s, 6H, —CH$_3$)

Example 2 (Microcapsules of polyurethane loaded with 50% DMP) δ (ppm): 7.73-7.69 (d, 4 Ar—H), 3.82 (s, 6H, —CH$_3$), 5.77 (d, 1H, —NH), 5.57 (d, 1H, —NH), 2.75-0.76 (combined signals corresponding to —CH$_3$, —CH$_2$, —CH of isosorbide and IPDI).

$^1$H-NMR spectrum of polyurethane microcapsules loaded with DMP exhibited the characteristic peaks of the DMP.

3. Extraction Studies:

Extraction of the DMP was carried out to determine the actual loading of DMP in the capsules i.e. encapsulation efficiency. Following procedure was used for the extraction studies: Approximately 0.5 g of sample was taken and transferred to 100 mL round bottom flask. 25-30 mL methanol was added to this flask and refluxed at 60-70° C. for 8 h. The mixture was cooled to 27° C. and filtered through Grade-3 sintered crucible. The residue was washed with 25-30 mL methanol and filtrate was transferred to 100 mL volumetric flask then diluted with methanol. From this 100 mL flask, 1.0 mL of solution was transferred to 25 mL volumetric flask and diluted with methanol. This last dilution was performed thrice. The absorbance of the diluted solution was determined at 276 nm ($\lambda_{max}$ for DMP) on UV spectrophotometer (Hitachi-Model 220).

The concentration of DMP determined using calibration slope (0.01) using following formula:

$$\% \, DMP = \frac{\text{Absorbance} * 250}{0.01 * \text{Weight of sample in mg}}$$

The encapsulation efficiencies of MICs of the types pristine, containing 2% NC and 4% NC were found to be 93.24%, 80.28%, 70.26%, respectively. This indicated that DMP content obtained by extraction studies is in good agreement with theoretical loading.

4. Release Rate Studies

A perfect sink condition was followed to carry out release study of DMP from MICs. A sufficient quantity of MICs was taken in 400 mL distilled water in 500 mL beaker kept in thermostatic bath maintained at 30±0.1° C. The release mixture was stirred at 200 rpm using over head stirrer fitted with rod having paddle type blades. At a specific time interval, 10 mL aliquots were taken out using graduated 10 mL pipette having cotton plug at the tip to avoid entering of capsules in the aliquot. The amount of DMP release from MICs was determined by measurement of absorbance at the maximum wavelength of absorbance ($\lambda$max 276 nm). 10 mL of eluting solvent (water) was added to the beaker to make total volume at 400 mL. The release rate experiments for each sample were carried out in duplicate and average of cumulative release obtained from two sets of experiments was noted. FIG. 8 shows the release rate study of microcapsules obtained in Example 2, Example 3 and Example 4. The microcapsules containing 2% nanocellulose exhibited significant reduction in the release rate of DMP in the first 500 min as compared to MICs containing 4% nanocellulose.

Advantages of Invention

- Use of renewable resource materials for the preparation of bio-based polyurethane microcapsules by using interfacial polymerization.
- Higher encapsulation efficiencies in the range 70-95% and lower release rate.
- Use of aliphatic diisocyanate since polyurethanes based on aliphatic isocyanates are considered as more biocompatible than polyurethanes based on aromatic isocyanates because the products of degradation of aromatic isocyanates are toxic, such as aromatic amines.

We claim:

1. A partially bio-based polyurethane microcapsule for sustained release of an active ingredient comprising;
   i) a core containing at least one active ingredient selected from the group consisting of dimethyl phthalate, N,N-Diethyl-meta-toluamide (DEET), Ibuprofen, Diuron, Zinc Pyrithione, Irgarol, and 4-Anisaldehyde; and
   ii) a bio-compatible polymeric shell consisting of (a) a bio-based aliphatic diol, (b) an aliphatic diisocyanate, (c) a cross linker and (d) an additive; wherein the bio-based aliphatic diol is selected from the group consisting of isosorbide, 1,3-propane diol, 1,4-butane diol, 2,3-butane diol, and 1,6-hexane diol and the aliphatic diisocyanate is selected from the group consisting of 1,6 Hexamethylene diisocyanates (HMDI), Isophorone diisocyanate (IPDI), pentamethylene diisocyanates (PDI), and 4,4'-Diisocyanatodicyclohexylmethane ($H_{12}$ MDI); wherein said additive is selected from the group consisting of nanocellulose, nanoclay, nanosilica and carbon nanotube (CNT);

wherein, the mole ratio of diisocyanate to hydroxyl groups present in aliphatic diol is 1.2:1;

and wherein, the partially bio-based polyurethane microcapsule has an encapsulation efficiency of 70-95%.

2. The partially bio-based polyurethane microcapsule as claimed in claim 1, wherein said cross linker is selected from the group consisting of glycerol, trimethylol propane (TMP), triethylenetetramine (TETA) and trimethylol ethane (TME).

3. A process for the synthesis of a partially bio-based polyurethane microcapsule, as claimed in claim 1, using interfacial polycondensation comprising the steps of
   a) preparing a solution of additive in water by overnight stirring followed by homogenization to obtain a dispersion;
   b) adding the dispersion prepared in step (a) to a solution of a surfactant in water followed by sonicating to obtain a continuous phase;
   c) emulsifying a solution of aliphatic diisocyanate and an active ingredient in the continuous phase obtained in step (b) to obtain a first mixture;
   d) preparing a second mixture of a bio-based aliphatic diol, a cross-linker and a catalyst in water;
   e) adding the second mixture obtained in step (d) dropwise to the first mixture obtained in step (c) to obtain a reaction mixture; and
   f) stirring the reaction mixture followed by centrifugation and filtration to obtain the partially bio-based and bio-compatible polyurethane microcapsules.

4. The process as claimed in claim 3, wherein said surfactant is selected from the group consisting of polyvinyl pyrrolidone (PVP K-90), polyvinyl pyrrolidone (PVP K-30), polyvinyl alcohol (PVA), Tween 80, sodium lignosulphonate (SLS) and sodium dodecyl sulfate (SDS).

5. The process as claimed in claim 3, wherein said catalyst is selected from the group consisting of 1,4-Diazabicyclo[2.2.2]octane (DABCO), and DibutyltinDilaurate (DBTDL).

6. The process as claimed in claim 3, wherein said additive is selected from the group consisting of nanocellulose, nanoclay, nanosilica and carbon nanotube (CNT).

7. The process as claimed in claim 3, wherein said bio-based aliphatic diol is selected from the group consisting of isosorbide, 1,3-propane diol, 1,4-butane diol, 2,3-butane diol, and 1,6-hexane diol.

8. The process as claimed in claim 3, wherein said aliphatic diisocyanate is selected from the group consisting of 1,6 (HMDI), Isophorone diisocyanate (IPDI), pentamethylene diisocyanates (PDI), and 4,4'-Diisocyanatodicyclohexylmethane ($H_{12}$ MDI).

9. The process as claimed in claim 3, wherein said cross linker is selected from the group consisting of glycerol, trimethylol propane (TMP), triethylenetetramine (TETA) and trimethylol ethane (TME).

10. The process as claimed in claim 3, wherein the active ingredient is selected from the group consisting of dimethyl phthalate, N,N-Diethyl-meta-toluamide (DEET), Ibuprofen, Diuron, Zinc Pyrithione, Irgarol, and 4-Anisaldehyde.

* * * * *